(12) United States Patent
Ishibashi et al.

(10) Patent No.: US 10,086,634 B2
(45) Date of Patent: Oct. 2, 2018

(54) HEAT-SENSITIVE RECORDING MATERIAL

(71) Applicant: SANKO CO., LTD., Fukuoka (JP)

(72) Inventors: Yoshimi Ishibashi, Osaka (JP); Ryoichi Kinishi, Osaka (JP); Yoshito Nakagawa, Osaka (JP)

(73) Assignee: SANKO CO., LTD., Fukuoka (JP)

( * ) Notice: Subject to any disclaimer, the term of this patent is extended or adjusted under 35 U.S.C. 154(b) by 0 days.

(21) Appl. No.: 15/742,067

(22) PCT Filed: Sep. 13, 2016

(86) PCT No.: PCT/JP2016/076929
§ 371 (c)(1),
(2) Date: Jan. 5, 2018

(87) PCT Pub. No.: WO2017/047572
PCT Pub. Date: Mar. 23, 2017

(65) Prior Publication Data
US 2018/0194151 A1    Jul. 12, 2018

(30) Foreign Application Priority Data

Sep. 18, 2015 (JP) ................................ 2015-185024
Mar. 3, 2016 (JP) ................................ 2016-041569
Jul. 15, 2016 (JP) ................................ 2016-140814

(51) Int. Cl.
*B41M 5/333* (2006.01)
*C07C 237/40* (2006.01)
*C07C 311/19* (2006.01)
*C07C 275/42* (2006.01)
*C07C 311/51* (2006.01)
*C07C 323/59* (2006.01)

(52) U.S. Cl.
CPC ......... *B41M 5/3333* (2013.01); *C07C 237/40* (2013.01); *C07C 275/42* (2013.01); *C07C 311/19* (2013.01); *C07C 311/51* (2013.01); *C07C 323/59* (2013.01)

(58) Field of Classification Search
CPC .... B41M 5/333; B41M 5/3333; B41M 5/337; B41M 5/3375; C07C 237/40; C07C 275/42; C07C 311/51; C07C 323/59

USPC ................................................. 503/209, 216
See application file for complete search history.

(56) References Cited

U.S. PATENT DOCUMENTS

| 5,868,821 A | 2/1999 | Torii et al. |
| 2015/0367663 A1 | 12/2015 | Yamane et al. |

FOREIGN PATENT DOCUMENTS

| JP | H05-147357 A | 6/1993 |
| JP | H06-032060 A | 2/1994 |
| JP | H07-109423 A | 4/1995 |
| JP | H09-290566 A | 11/1997 |
| JP | 2005-145935 A | 6/2005 |
| JP | 2005-254764 A | 9/2005 |
| JP | 2010-052137 A | 3/2010 |
| JP | 2015-003403 A | 1/2015 |

OTHER PUBLICATIONS

International Search Report dated Oct. 18, 2016 by the International Searching Authority for Patent Application No. PCT/JP2016/076929, which was filed on Sep. 13, 2016 and published as WO 2017/07572 on Mar. 23, 2017 (Inventor—Ishibashi et al.; Applicant—Sanko Co., Ltd.) (Original—4 pages // Translation—3 pages).

*Primary Examiner* — Bruce H Hess
(74) *Attorney, Agent, or Firm* — Ballard Spahr LLP

(57) ABSTRACT

A heat-sensitive recording material includes a heat-sensitive recording layer containing a basic dye and a developer and provided on a supporting body, in which the developer is at least one type of an N-substituted amino acid derivative represented by the following General Formula: $(R-X)_m-Y-(Z)_m \ldots (1)$ (In Formula (1), R represents an alkyl group or an aryl group which may have a substituent. X is a group bonded to the N-terminus of Y, and represents $-OCO-$, $-SO_2NHCO-$, $-NHCO-$, $-NHCS-$, or $-SO_2-$. Y represents an amino acid residue or a peptide residue. Z represents a group bonded to the C-terminus of Y and represents an OH group or an OR" group. When Y is an amino acid residue other than a cystine residue or when Y is a peptide residue not having a cystine residue, m=1, and when Y is a peptide residue having n cystine residues, m=n+1 and n is 1 or 2.)

4 Claims, No Drawings

HEAT-SENSITIVE RECORDING MATERIAL

CROSS-REFERENCE TO RELATED APPLICATIONS

This application is a U.S. National Phase Application of International Application No. PCT/JP2016/076929, filed Sep. 13, 2016, which claims priority to Japanese Application Nos. 2015-185024, filed Sep. 18, 2015; 2016-041569, filed Mar. 3, 2016; and 2016-140814, filed Jul. 15, 2016, each of which are hereby incorporated by reference in their entirety.

TECHNICAL FIELD

The present invention relates to a heat-sensitive recording material, and in particular, to a heat-sensitive recording material using an N-substituted amino acid derivative as a developer.

Priority is claimed on Japanese Patent Application No. 2015-185024, filed on Sep. 18, 2015 in Japan, Japanese Patent Application No. 2016-041569 filed on Mar. 3, 2016 in Japan, and Japanese Patent Application No. 2016-140814 filed on Jul. 15, 2016 in Japan, the contents of which are incorporated herein by reference.

BACKGROUND ART

In general, a heat-sensitive recording material in which heat energy (Joule heat) from a heat-sensitive head, heat pen, or the like is applied to a basic dye which is colorless or light-colored at room temperature and an organic developer to obtain a color recording is already widely put into practical use.

Examples of the performances required for the heat-sensitive recording material include the whiteness of the unprinted portion, the whiteness of the unprinted portion under various environmental conditions, the coloring density of the printed portion, the storage stability of the printed portion, and the like.

The storage stability of the printed portion means the performance in which loss of the printed image is not caused even in a case where the printed image is placed in a high humidity environment, a case where water is adhered thereto, a case where oil is adhered thereto, a case where a plasticizer is adhered thereto, or the like.

On the other hand, the required performances for prints formed by the heat-sensitive recording material largely depend on the dyes, developers, and sensitizers which are the main components of the heat-sensitive recording material and, in particular, the influence of the developer is large.

For this reason, synthetic compounds derived from petrochemicals such as phenolic compounds or sulfonylurea compounds have been proposed as developers satisfying the required performances described above. Among these, many phenolic compounds have been developed and put to practical use.

However, there are concerns of some phenolic compounds exhibiting endocrine disruption and therefore use thereof is recently being suppressed. For example, bisphenol A (2,2-bis(4-hydroxyphenyl)propane) has been used in large quantities as a raw material for polyester or as a developer for heat-sensitive paper; however, bisphenol A is classified as a Type II and a Type III Monitoring Chemical Substance in the Japanese Act on the Evaluation of Chemical Substances and Regulation of Their Manufacture, etc., before amendment and as a priority assessment chemical substance in the same Act after amendment, furthermore, the use thereof has already been restricted in the EU, the United States, Canada. Japan, and the like due to suspicions of being an endocrine disrupting substance.

Bisphenol S(4,4'-dihydroxydiphenylsulfone) is registered as a designated chemical substance in the Japanese Act on the Evaluation of Chemical Substances and Regulation of Their Manufacture, etc., before amendment due to concerns of chromosomal abnormalities and the like and regulated as a Type II Monitoring Chemical Substance.

As a non-phenolic developer such as a sulfonylurea compound, the use of a synthetic compound such as 4,4'-diaminodiphenylalkane as a raw material has been proposed (Patent Document 1). The use of a non-phenolic developer using an acylated amino acid where the main raw material is a natural amino acid has been proposed (Patent Document 2). In addition, a heat-sensitive recording material which obtains an image by applying a browning reaction (Maillard reaction) by heating amino acids and saccharides has also been proposed (Patent Document 3).

CITATION LIST

Patent Literature

[Patent Document 1] Japanese Unexamined Patent Application, First Publication No. H05-147357
[Patent Document 2] Japanese Unexamined Patent Application, First Publication No. H07-109423
[Patent Document 3] Japanese Unexamined Patent Application, First Publication No. 2005-254764

SUMMARY OF INVENTION

Technical Problem

However, the sulfonylurea compound proposed in Patent Document 1 has a problem in that a synthetic compound having a molecular structure similar to that of bisphenol A is used as a raw material for a constituent component, and the sulfonylurea compound does not sufficiently meet the performances required as a developer for a heat-sensitive recording material.

The use of a developer using an acylated amino acid having a natural amino acid as a main raw material in Patent Document 2 is not categorized as use of a substance causing endocrine disruption as described above. However, in terms of the coloring density, whiteness, and various types of storage stability of the unprinted portion, the printed portion, and the like, the quality performance thereof does not reach the performance required as a developer for a heat-sensitive recording material.

The proposal for obtaining an image by applying a browning reaction (Maillard reaction) by heating the amino acids and saccharides of Patent Document 3 does not satisfy the performance required as a developer.

The present invention has been made in view of the circumstances described above and has an object of providing a heat-sensitive recording material using an N-substituted amino acid derivative which satisfies the performances required as a developer such as coloring density, whiteness, and storage stability of a printed portion and for which there is no concern about an endocrine disrupting action.

Solution to Problem

The inventors of the present application carried out research from the viewpoint of whether it is possible to use amino acids which are also foods as a developer for a heat-sensitive recording material. As a result, it was found that, since the basic amino group and the acidic carboxyl group coexist in the same molecule and are neutralized in the molecule, the amino acid does not impart a color even when it comes in contact with the basic dye. The inventors of the present application completed the present invention by introducing a functional group, which contributes to the required performance and developing ability of a developer of a heat-sensitive recording material, as a protecting group of an amino group of an amino acid so as to eliminate the intramolecular neutralization and strongly express the developing ability of the amino acid and, in particular, by using an N-substituted amino acid derivative in which a raw material thereof is a natural amino acid, as a developer.

The present invention includes the following aspects.

[1] A heat-sensitive recording material including a heat-sensitive recording layer provided on a supporting body, the heat-sensitive recording layer containing a basic dye which is colorless or light-colored at room temperature and a developer capable of expressing a color through contact with the dye by heating, wherein the developer is at least one type of an N-substituted amino acid derivative represented by the following General Formula (1):

In Formula (1), R represents an alkyl group which may have a substituent of an aryl group having 6 to 10 carbon atoms, an alkoxy group having 1 to 8 carbon atoms, or an isocyanate group, or an aryl group which may have a substituent of an alkyl group having 1 to 8 carbon atoms, an aralkyl group having 7 to 11 carbon atoms, an aryl group having 6 to 10 carbon atoms, an alkoxy group having 1 to 8 carbon atoms, or an isocyanate group.

X is a group bonded to an N-terminus of Y and represents —OCO—, —SO$_2$NHCO—, —NHCO—, —NHCS—, or —SO$_2$—.

Y represents an amino acid residue or a peptide residue and the OH group of a serine residue, a threonine residue, an aspartic acid residue, a glutamic acid residue, or a tyrosine residue in the Y group may be substituted with an OR group or an OR" group, an SH group of a cysteine residue may be substituted with an SR group or an SR" group, an NH group of a histidine residue may be substituted with an NR group or an NR' group, an NH$_2$ group of a lysine residue or an ornithine residue may be substituted with an NHR group or an NHR' group, R' represents an amino protecting group, and R" represents a carboxy protecting group.

Z is a group bonded to the C-terminus of Y and represents an OH group or an OR" group. A plurality of R, R', and R" groups may be the same as or different from each other and may be bonded to each other to form a ring.

When Y is an amino acid residue other than a cystine residue or when Y is a peptide residue not having a cystine residue, m=1, and when Y is a peptide residue having n cystine residues, m=n+1 and n is 1 or 2.

[2] The heat-sensitive recording material according to [1] mentioned above, in which the developer is at least one type selected from the group consisting of N-(m-tolylaminocarbonyl)-phenylalanine, N-(m-tolylaminocarbonyl)-methionine, N-(p-tolylaminocarbonyl)-methionine, N-(phenylaminocarbonyl)-methionine, N-(m-tolylaminocarbonyl)-valine, N-(m-tolylaminocarbonyl)-phenylglycine, and N-(m-tolylaminocarbonyl)-tyrosine.

[3] The heat-sensitive recording material according to [1] or [2] mentioned above, in which, the heat-sensitive recording layer contains, as a storage stabilizer, at least one type or more selected from 1,1,3-tris(2-methyl-4-hydroxy-5-tert-butylphenyl)butane, 1,1,3-tris(2-methyl-4-hydroxy-5-cyclohexylphenyl)butane, 4,4'-bis[(4-methyl-3-phenoxycarbonylaminophenyl) ureido] diphenylsulfone, and a diphenylsulfone cross-linking type compound represented by General Formula (2).

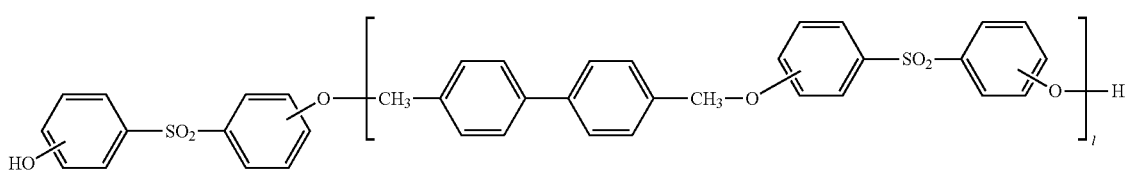

In the formula, 1 represents an integer ranging from 1 to 6.

[4] The heat-sensitive recording material according to [3] mentioned above, in which the amount of the storage stabilizer ranges from 2.5 to 100 parts by mass with respect to 100 parts by mass of the developer.

Advantageous Effects of Invention

The developer which is the derivative with the aforementioned N-substituted amino acid as the raw material, according to the present invention, makes it possible to provide a heat-sensitive recording material which satisfies the performance requirements for heat-sensitive recording materials to a degree equal to the developers of the related art and which is safe without an endocrine disrupting action or the like.

DESCRIPTION OF EMBODIMENTS

In a heat-sensitive recording material according to the present embodiment, a heat-sensitive recording layer, containing a basic dye which is colorless or light-colored at room temperature and a developer capable of expressing a color through contact with the dye by heating, is provided on a supporting body.

A heat-sensitive recording material according to one embodiment of the present invention is provided with a heat-sensitive recording layer provided on a supporting body. The heat-sensitive recording layer contains a basic dye which is colorless or light-colored at room temperature and a developer capable of expressing a color through contact with the dye by heating. The developer is at least one type of an N-substituted amino acid derivative represented by General Formula (1) shown below. The heat-sensitive recording layer of the heat-sensitive recording material according to one embodiment of the present invention is formed by preparing a coating liquid obtained by adding the aforementioned basic dye, the aforementioned developer represented by the general formula, a binder, a sensitizer, a filler, a lubricant, various other additives, and the like, and applying the obtained coating liquid onto a supporting body such as paper, plastic film, or processed paper.

In the heat-sensitive recording material according to one embodiment of the present invention, the developer is at least one type of N-substituted amino acid derivative represented by the following General Formula (1).

$$(R-X)_m-Y-(Z)_m \quad (1)$$

In Formula (1), R represents an alkyl group which may have a substituent of an aryl group having 6 to 10 carbon atoms, an alkoxy group having 1 to 8 carbon atoms, or an isocyanate group, or an aryl group which may have a substituent of an alkyl group having 1 to 8 carbon atoms, an aralkyl group having 7 to 11 carbon atoms, an aryl group having 6 to 10 carbon atoms, an alkoxy group having 1 to 8 carbon atoms, or an isocyanate group.

Examples of alkyl groups include a methyl group, an ethyl group, a propyl group, an isopropyl group, a butyl group, an isobutyl group, a sec-butyl group, a pentyl group, an isoamyl group, a neopentyl group, a 2-methylbutyl group, a hexyl group, an isohexyl group, a 4-methylpentyl group, and the like.

Examples of the alkyl group which may have an aryl group having 6 to 10 carbon atoms (aralkyl group) include a benzyl group, a phenethyl group, an o-tolylmethyl group, an m-tolylmethyl group, a p-tolylmethyl group, an o-tolylethyl group, an m-tolylethyl group, a p-tolylethyl group, and the like. Examples of the aralkyl group having 7 to 11 carbon atoms include a benzyl group, a phenethyl group, and the like.

Examples of aryl groups include a phenyl group, a naphthyl group, and the like. Examples of aryl groups which may have an alkyl group having 1 to 8 carbon atoms include an o-tolyl group, an m-tolyl group, a p-tolyl group, a 1-ethylphenyl group, a 2-ethylphenyl group, a 3-ethylphenyl group, a 1-propylphenyl group, a 2-propylphenyl group, a 3-propylphenyl group, a 1-butylphenyl group, a 2-butylphenyl group, a 3-butylphenyl group, a 1-pentylphenyl group, a 2-pentylphenyl group, a 3-pentylphenyl group, and the like. Examples of aryl groups having 6 to 10 carbon atoms include a phenyl group, an o-tolyl group, an m-tolyl group, a p-tolyl group, a 1-ethylphenyl group, a 2-ethylphenyl group, a 3-ethylphenyl group, and the like.

Examples of the aryl group which may have a substituent of an aralkyl group having 7 to 11 carbon atoms or an aryl group having 6 to 10 carbon atoms include a biphenyl group, a 3,3'-dimethylbiphenyl group, a p-benzylbiphenyl group, and the like. Examples of the aryl group which may have a substituent of an alkoxy group having 1 to 8 carbon atoms include a 6-methoxyphenyl group, and the like.

X is a group bonded to the N-terminus of Y and represents —OCO—, —SO$_2$NHCO—. —NHCO—, —NHCS—, or —SO$_2$— (sulfonyl group).

Y represents an amino acid residue or a peptide residue and an OH group of a serine residue, a threonine residue, an aspartic acid residue, a glutamic acid residue, or a tyrosine residue in the Y group may be substituted with an OR group or an OR" group, an SH group of the cysteine residue may be substituted with an SR group or an SR" group, an NH group of the histidine residue may be substituted with an NR group or an NR' group, the NH$_2$ group of a lysine residue or an ornithine residue may be substituted with an NHR group or an NHR' group, R' represents an amino protecting group, and R" represents a carboxy protecting group.

Examples of the amino protecting group (R' group) which protects the NH group of a histidine residue in the Y group, or protects the NH$_2$ group of a lysine residue or an ornithine residue include an RX group and other examples thereof include an acyl group, or an alkyl group. Examples of the carboxy protecting group (R" group) for protecting an aspartic acid residue or a glutamic acid residue in the Y group include an alkoxy group, an aryloxy group, an amino group, an alkylamino group, an arylamino group, and the like. In addition, examples of the protecting group for the OH group of a serine residue, a threonine residue, or a tyrosine residue, or the SH group of a cysteine residue in the Y group include the aforementioned carboxy protecting group (R" group).

Z is a group bonded to the C-terminus of Y and represents an OH group or an OR" group.

A plurality of R, R' and R" groups may be the same as or different from each other and may be bonded to each other to form a ring.

When Y is an amino acid residue other than a cystine residue or when Y is a peptide residue not having a cystine residue, m=1, and when Y is a peptide residue having n cystine residues, m=n+1 and n is 1 or 2.

It is possible to easily manufacture the N-substituted amino acid derivative represented by the aforementioned general formula from an amino acid or an amino acid derivative and a sulfonic acid chloride, an isocyanate compound, or the like by applying a known method such as a Schotten-Baumann reaction.

The amino acids, peptides, and esters and amides thereof used as constituent components of the compound represented by the aforementioned general formula may be in an L form, a D form, or a DL form. A natural amino acid, an unnatural amino acid, an α-amino acid, or a β-one may be used. The esters are alkyl esters with 1 to 4 carbon atoms, aryl esters, aralkyl esters, and the amides are amides, alkyl substituted amides, aryl substituted amides, and the like.

Specific examples include glycine, ester derivatives such as glycine methyl ester, glycine ethyl ester, glycine t-butyl ester, glycine phenyl ester, glycine p-cresyl ester, glycine m-cresyl ester, and glycine benzyl ester, amide derivatives such as glycine amide, N'-methylglycine amide, and glycylanilide, phenylglycine, ester derivatives such as phenylglycine methyl ester, phenylglycine ethyl ester, and phenylglycine benzyl ester, phenylglycinamide, alanine, ester derivatives such as alanine methyl ester, alanine ethyl ester, and alanine benzyl ester, alanine amide, phenyl alanine, naphthyl alanine, ester derivatives such as phenyl alanine methyl ester, phenyl alanine ethyl ester, and phenyl alanine benzyl ester, amide derivatives such as phenylalanine amide, N'-methylphenylalanine amide, and phenylalanylanilide, valine, ester derivatives such as valine methyl ester, valine methyl ester, valine isopropyl ester, valine t-butyl ester, and valine benzyl ester, valine amide, leucine, leucine methyl ester, isoleucine, serine, o-substituted serines such as o-methyl serine, and o-benzyl serine, ester derivatives such as serine methyl ester and serine benzyl ester, threonine, o-substituted threonine such as o-methyl threonine, and o-benzyl threonine, ester derivatives such as threonine methyl ester and threonine t-butyl ester, tyrosine, o-substituted tyrosine such as o-methoxytyrosine, o-benzyloxy tyrosine, and tyrosine, 3-(3',4'-dihydroxyphenyl) alanine (DOPA), ester derivatives such as tyrosine methyl ester, and tyrosine benzyl ester, tyrosine amide, proline, hydroxyproline, ester derivatives such as proline methyl ester, proline t-butyl ester, and proline benzyl ester, proline amide, lysine, ornithine, ester derivatives such as lysine methyl ester, lysine ethyl ester, lysine benzyl ester, ornithine methyl ester, ornithine ethyl ester, and omithine benzyl ester, arginine, arginine methyl ester, arginine ethyl ester, histidine, histidine methyl ester, tryptophan, tryptophan methyl ester, tryptophan benzyl ester, tryptophan amide, cysteine, cystine, S-substituted cysteines such as S-methyl cysteine, S-ethyl cysteine, S-benzyl cysteine, and S-phenyl cysteine, ester derivatives such as cysteine methyl ester and cysteine benzyl ester, S-oxidized derivatives such as cysteine sulfoxide and sulfone, methionine, S-oxidized derivatives such as methionine sulfoxide, and methionine sulfone, ester derivatives such as methionine methyl ester and methionine benzyl ester, methionine amide, aspartic acid, ester derivatives such as aspartic acid methyl ester, aspartic acid ethyl ester, and aspartic acid benzyl ester, asparagine, glutamic acid, ester derivatives such as glutamic acid methyl ester, glutamic acid ethyl ester, and glutamic acid benzyl ester, and glutamine.

Furthermore, examples may include an amino acid such as homoserine, homocysteine, or norleucine, or a derivative thereof. In addition, aminocarboxylic acids with 1 to 8 carbon atoms such as β-alanine, 5-aminovaleric acid, and 7-aminoheptanoic acid can also be selected.

Examples of peptides include glycylglycine, glycylglycine methyl ester, glycylglycinamide, glycylalanine, glycylalanine methyl ester, glycylvaline, glycylleucine, glycylphenylalanine, glycylphenylalanine methyl ester, glycylphenylalaninamide, glycylproline, alanylalanine, alanylproline, alanylmethionine, alanylmethionine methyl ester, alanylphenylalanine, glycylglycylglycine, and the like.

The compound represented by the aforementioned general formula is an amino group-protected amino acid or peptide or a derivative thereof, and the protecting group thereof is widely used in the field of amino acid chemistry or peptide synthesis chemistry.

Examples of the functional group (—XNH— group) formed by the N-substituent of the N-substituted amino acid derivative represented by the aforementioned General Formula (1) in the heat-sensitive recording material according to one embodiment of the present invention include a sulfonylamino group, a urethane group, a (thio)urea group (ureido), and a sulfonylurea group, and these functional groups, for example, sulfonylamino groups are derived from alkanesulfonyl chloride or arylsulfonyl chloride. The urethane group is derived from a chloroformic acid ester such as chloroformic acid t-butyl ester and chloroformic acid benzyl ester, or a carbonic acid ester such as dimethyl carbonate. The (thio)urea group is derived from an iso(thio)cyanic acid ester such as phenyl iso(thio)cyanate. Sulfonylurea is derived from a sulfonylurea such as toluenesulfonyl isocyanate.

Specific examples of the compound (X1) forming a sulfonylamino group include chlorides such as methanesulfonyl chloride, ethanesulfonyl chloride, propanesulfonyl chloride, butanesulfonyl chloride, benzenesulfonyl chloride, p-toluenesulfonyl chloride, m-toluenesulfonyl chloride, o-toluenesulfonyl chloride, p-methoxybenzenesulfonyl chloride, p-xylenesulfonyl chloride, m-xylenesulfonyl chloride, mesitylenesulfonyl chloride, 1-naphthalenesulfonyl chloride, and 2-naphthalenesulfonyl chloride, bromides, iodides, and the like.

Examples of the compound (X2) forming a urethane group include halogenated formic acid esters such as chloroformic acid methyl ester, chloroformic acid ethyl ester, chloroformic acid t-butyl ester, chloroformic acid benzyl ester, and chloroformic acid phenyl ester, carbonate esters such as dimethyl carbonate, diethyl carbonate, diphenyl carbonate, and dibenzyl carbonate, and the like.

Examples of the compound (X3) forming a (thio)urea group include butyl isocyanate, hexyl isocyanate, hexamethylene 1,6-diisocyanate, benzyl isocyanate, phenyl isocyanate, p-tolyl isocyanate, m-tolyl isocyanate, o-tolyl isocyanate, 1-naphthyl isocyanate, 2-naphthyl isocyanate, phenylene 1,4-diisocyanate, phenylene 1,3-diisocyanate, tolylene 2,4-diisocyanate, tolylene 2,6-diisocyanate, p-xylylene diisocyanate, m-xylylenene diisocyanate, naphthalene 1,5-diisocyanate, 4,4'-diisocyanato-3,3'-dimethylbiphenyl, methylenediphenyl 4,4'-diisocyanate, 4,4'-diisocyanato-3,3'-dimethyl diphenyl methane, phenyl isothiocyanate, m-tolyl isothiocyanate, p-tolyl isothiocyanate, and the like.

Examples of the compound (X4) forming a sulfonylurea group include benzenesulfonyl isocyanate, p-toluenesulfonyl isocyanate, and the like.

Examples of the N-substituted amino acid derivative obtained by using the compound (X1) forming a sulfonylamino group in the aforementioned General Formula (1) include N—(C1-C8 alkane) sulfonyl-amino acids, esters, and amides thereof such as N-methanesulfonyl-glycine, N-methanesulfonyl-glycine benzyl ester, N-methanesulfonyl-glycine amide, N-methanesulfonyl-valine. N-methanesulfonyl-phenylalanine, N-methanesulfonyl-phenylalanine methyl ester. N-methanesulfonyl-phenylalanine benzyl ester, N-methanesulfonyl-β-alanine, N-methanesulfonyl-β-alanine methyl ester, N-ethanesulfonyl-leucine, N-propanesulfonyl-methionine, N-methanesulfonyl-asparagine, and N-methanesulfonyl-glutamine, N-arylsulfonyl-amino acids, esters, and amides such as N-benzenesulfonyl-glycine, N-benzenesulfonyl-glycine methyl ester, N-benzenesulfonyl-glycinamide, N-benzenesulfonyl-methionine methyl ester, N-benzenesulfonyl-cysteine S-benzyl, N-(p-toluenesulfonyl)-glycine, N-(p-toluenesulfonyl)-alanine, N-(p-toluenesulfonyl)-β-alanine, N-p-toluenesulfonyl)-phenyl alanine, N-(p-toluenesulfonyl)-phenylalanine methyl ester, N-(p-toluenesulfonyl)-phenylalanine benzyl ester, N-(p-toluenesulfonyl)-methionine, N-(p-toluenesulfonyl)-methionine benzyl ester, N-(m-toluenesulfonyl)-isoleucine, 3-N-(o-toluenesulfonyl) aminocaproic acid, N-(2,4-xylenesulfonyl)-alanine, N-(2,4,6-mesitylenesulfonyl)-serine, N-(p-ethylbenzenesulfonyl)-threonine, N,N'-di(p-t-butylbenzenesulfonyl)-lysine, N,N'-di(p-t-butylbenzenesulfonyl)-ornithine, N-(1-naphthalenesulfonyl)-tryptophan, and N-2-naphthalene sulfonyl-asparagine, N-aralkylsulfonyl-amino acids, esters, and amides such as N-benzylsulfonyl-valine, N-benzylsulfonyl-tyrosine, and N-benzylsulfonyl-phenyl glycine, and the like.

As the N-substituted amino acid derivative obtained by using the compound (X3) forming a urea group in the aforementioned General Formula (1), it is suitable to use at least one type selected from the group consisting of N-phenylaminocarbonyl-glycine. N-phenylaminocarbonyl-glycine methyl ester. N-phenylaminocarbonyl-glycine benzyl ester, N-phenylaminocarbonyl-glycinamide, N-phenylaminocarbonyl-alanine, N-phenylaminocarbonyl-alanine-methyl ester, N-phenylaminocarbonyl-β-alanine, N-phenylaminocarbonyl-methionine, N-phenylaminocarbonyl-methionine methyl ester, N-phenylaminocarbonyl-glutamine, N,N'-di(phenylaminocarbonyl)-lysine, N,N'-di(phenylaminocarbonyl)-omithine, N-phenylaminocarbonyl-phenylalanine, N-phenylaminocarbonyl-norvaline, N-(p-tolylaminocarbonyl)-glycine, N-(p-tolylaminocarbonyl)-alanine, N-(p-tolylaminocarbonyl)-valine, N-(p-tolylaminocarbonyl)-phenylalanine, N-(p-tolylaminocarbonyl)-cysteine-S-benzyl, N-(p-tolylaminocarbonyl)-methionine, N-(p-tolylaminocarbonyl)-glutamic acid, N-(p-tolylaminocarbonyl)-glutamine, N-(m-tolylaminocarbonyl)-glycine, N-(p-tolylaminocarbonyl)-glycyl glycine, N-(p-tolylaminocarbonyl)-glycylglycyl glycine. N-(m-tolylaminocarbonyl)-glycyl alanine, N-(m-tolylaminocarbonyl)-leucyl alanine. N-(m-tolylaminocarbonyl)-methionine, N-(m-tolylaminocarbonyl)-methionine sulfone, N-(m-tolylaminocarbonyl)-valine, N-(m-tolylaminocarbonyl)-tyrosine, N-(m-tolylaminocarbonyl)-tyrosine methyl ester, N-(m-tolylaminocarbonyl)-phenylalanine, N-(m-tolylaminocarbonyl)-methionine, N-(m-tolylaminocarbonyl)-valine, N-(m-tolylaminocarbonyl)-phenyl glycine, N-phenyl glycine, N-(3-isopropenyl-α,α-dimethylbenzyl) aminocarbonyl-methionine, and N-(m-tolylaminocarbonyl)-tyrosine.

Examples thereof include N-(m-tolylaminocarbonyl)-phenylalanine methyl ester, N-(m-tolylaminocarbonyl)-phenylalanine ethyl ester. N-(m-tolylaminocarbonyl)-phenylalanine benzyl ester, N-(m-tolylaminocarbonyl)-β-phenylalanine amide, N,N'-di(m-tolylaminocarbonyl)-lysine, N,N'-di(m-tolylaminocarbonyl)-lysine methyl ester, N,N'-di(m-tolylaminocarbonyl)-omithine, N,N'-di(m-tolylaminocarbonyl)-omithine methyl ester, N-(m-tolylaminocarbonyl)-glutamic acid, N-(o-tolylaminocarbonyl)-alanine, N-(o-tolylaminocarbonyl)-homoserine, N-(o-tolylaminocarbonyl)-valine, 1,6-hexamethylene bis(N-aminocarbonyl-phenyl alanine), 2,4-phenylene bis(N-aminocarbonyl-phenyl alanine), 1,3-tolylene bis(N-aminocarbonyl-phenyl glycine), and the like.

Examples of the N-substituted amino acid derivative obtained by using the compound (X3) forming a thiourea group in the aforementioned General Formula (1) include N-phenylaminothiocarbonyl-phenylalanine, N-phenylaminothiocarbonyl-phenylalanine methyl ester. N-phenylaminothiocarbonyl-valine isopropyl ester. N-phenylaminothiocarbonyl-tyrosine methyl ester, N-phenylaminothiocarbonyl-methionine methyl ester, N-phenylaminothiocarbonyl-glycylglycine, N-phenylaminothiocarbonyl-glycylalanine, N-m-tolylaminothiocarbonyl-phenylalanine, N-m-tolylaminothiocarbonyl-phenylalanine benzyl ester, N-m-tolylamidothiocarbonyl-phenylalanine amide, N-m-tolylaminothiocarbonyl-valine, N-m-tolylaminothiocarbonyl-valine isopropyl ester, N-m-tolylaminothiocarbonyl-methionine methyl ester, N-m-tolylaminothiocarbonyl-glycylglycine, N-p-tolylaminothiocarbonyl-phenylalanine, N-p-tolylaminothiocarbonyl-phenylalanine benzyl ester, N-p-tolylaminothiocarbonyl-phenylalaninamide, N-p-tolylaminothiocarbonyl-valine, N-p-tolylaminothiocarbonyl-valine isopropyl ester, N-p-tolylaminothiocarbonyl-methionine methyl ester, N-p-tolylaminothiocarbonyl-glycylglycine, and the like.

Examples of the N-substituted amino acid derivative obtained by using the compound (X2) forming a urethane group in the aforementioned General Formula (1) include N-benzyloxycarbonyl-glycine. N-benzyloxycarbonyl-phenylglycine, N-benzyloxycarbonyl-valine, N-benzyloxycarbonyl-methionine, N-benzyloxycarbonyl-tyrosine, N-benzyloxycarbonyl-hydroxyproline, N-benzyloxycarbonyl-arginine, N-benzyloxycarbonyl-glycine, N-t-butoxycarbonyl-proline, N-t-butoxycarbonyl-glycine, N-t-butoxycarbonyl-phenylalanine, N-t-butoxycarbonyl-tryptophan, N-t-butoxycarbonyl-tyrosine, N-t-butoxycarbonyl-glutamic acid, and the like.

Examples of the N-substituted amino acid derivative obtained by using the compound (X4) forming a sulfonylurea group in the aforementioned General Formula (1) include N-(p-toluenesulfonylamino carbonyl)-glycine, N-(p-toluenesulfonylamino carbonyl)-phenylalanine, N-(p-toluenesulfonylamino carbonyl)-phenylalanine methyl ester, N-(p-toluenesulfonylamino carbonyl)-phenylalanine ethyl ester, N-(p-toluenesulfonylamino carbonyl)-phenylalanine amide, N-(p-toluenesulfonylamino carbonyl)-β-alanine, N-(p-toluenesulfonylaminocarbonyl)-β-alanine methyl ester, N-(p-toluenesulfonylamino carbonyl)-methionine methyl ester, N-(p-toluenesulfonylamino carbonyl)-leucine, N,N'-di(p-toluenesulfonylamino carbonyl)-lysine methyl ester, N,N'-di(p-toluenesulfonylamino carbonyl)-omithine methyl ester, and the like.

The N-substituted amino acid derivative obtained by using a diisocyanate compound such as hexamethylene 1,6-diisocyanate, phenylene 1,4-diisocyanate, phenylene 1,3-diisocyanate, tolylene 2,4-diisocyanate, tolylene 2,6-diisocyanate, p-xylylene diisocyanate, m-xylylene diisocyanate, naphthalene 1,5-diisocyanate, 4,4'-diisocyanato-3,3'-dimethylbiphenyl, methylene diphenyl 4,4'-diisocyanate, and 4,4'-diisocyanato-3,3'-dimethyldiphenylmethane may have an isocyanate group as an R group, and may form a ring by reacting the OH group of a serine residue, a threonine residue, an aspartic acid residue, a glutamic acid residue, or a tyrosine residue, the SH group of a cysteine residue, the NH group of a histidine residue, or the $NH_2$ group of a lysine residue or an omithine residue, in the Y group.

Examples of the amino protecting group (R' group) for protecting the NH group of the histidine residue or the $NH_2$ group of the lysine residue or the ornithine residue in the Y group of the N-substituted amino acid derivative represented by the aforementioned General Formula (1) in the heat-sensitive recording material according to one embodiment of the present invention include an RX group, and other examples thereof include an acyl group and an alkyl group. It is possible to introduce these amino protecting groups (R' groups) by a known method. For example, it is possible to introduce an acyl group using an acid anhydride. For example, it is possible to introduce the alkyl group with an alkyl halide such as trityl chloride in the presence of an amine or the like.

Examples of the carboxy protecting group (R" group) for protecting the aspartic acid residue or the glutamic acid residue in the Y group of the N-substituted amino acid derivative represented by the aforementioned General Formula (1) in the heat-sensitive recording material according to one embodiment of the present invention include an alkoxy group, an aryloxy group, an amino group, an alkylamino group, an arylamino group, and the like. In addition, examples of the protecting group for the OH group of the serine residue, the threonine residue, or the tyrosine residue in the Y group or the SH group of the cysteine residue include the carboxy protecting group (R''' group). It is possible to introduce these carboxy protecting groups (R''' group) by a known method.

Preferable N-substituted amino acid derivatives as a developer in the heat-sensitive recording material according to one embodiment of the present invention include N-allyl sulfonyl-amino acids such as N-(p-toluenesulfonyl)-glycine, N-(p-toluenesulfonyl)-alanine, and N-(p-toluenesulfonyl)-β-alanine, and N-amino carbonylamino acids such as N-phenylamino carbonyl-glycine, N-phenylamino carbonyl-valine, N-(m-tolylaminocarbonyl)-phenylalanine, N-(m-tolylaminocarbonyl)-cysteine-S-benzyl, N-(m-tolylaminocarbonyl)-methionine, N-(m- tolylaminocarbonyl)-tyrosine, N-(p-tolylaminocarbonyl)-phenylalanine, N-(p-tolylaminocarbonyl)-cysteine-S-benzyl, N-(p-tolylaminocarbonyl)-methionine, N-(p-tolylaminocarbonyl)-methionine, N-(phenylaminocarbonyl)-methionine, and N-(p-tolylaminocarbonyl)-tyrosine, and particularly preferably include N-(m-tolylaminocarbonyl)-phenylalanine, N-(m-tolylaminocarbonyl)-methionine, N-(p-tolylaminocarbonyl)-methionine, N-(phenylaminocarbonyl)-methionine, N-(m-tolylaminocarbonyl)-valine, N-(m-tolylaminocarbonyl)-phenylglycine, and N-(m-tolylaminocarbonyl)-tyrosine.

One type or two or more types of these N-substituted amino acid derivatives may be used in combination.

Furthermore, Z is preferably an OH group and X is preferably a —NHCO— group, and specifically, at least one type selected from the group consisting of N-(m-tolylaminocarbonyl)-phenylalanine, N-(m-tolylaminocarbonyl)-methionine, N-(p-tolylaminocarbonyl)-methionine, N-(phenylaminocarbonyl)-methionine, N-(m-tolylaminocarbonyl)-valine, N-(m-tolylaminocarbonyl)-phenylglycine, and N-(m-tolylaminocarbonyl)-tyrosine is suitably used as the N-substituted amino acid derivative.

The heat-sensitive recording material according to one embodiment of the present invention may be used in combination with a conventional developers as long as the effect of the present invention is not impaired.

Examples of basic dyes which are colorless or light-colored at room temperature in the heat-sensitive recording material according to one embodiment of the present invention include triphenylmethane-based compounds, fluoran-based compounds, diphenylmethane-based compounds, spiro-based compounds, fluorene-based compounds, and thiazine-based compounds, and it is possible to select from leuco dyes known in the related art.

For example, it is possible to select from 3,3-bis(p-dimethylamino phenyl)-6-dimethylamino phthalide, 3,3-bis(p-dimethylamino phenyl) phthalide, 3-(4-diethylamino-2-ethoxyphenyl)-3-(1-ethyl-2-methylindol-3-yl)-4-azaphthalide, 3,3-bis(P-methylamino phenyl)-6-dimethylamino phthalide, 3-diethylamino-7-dibenzylamino benzo[α]fluoran, 3-(1-ethyl-2-methylindol-3-yl)-3-(4-diethylamino-2-n-hexyloxyphenyl)-4-azaphthalide, 3-(1-ethyl-2-methylindol-3-yl)-3-(4-diethylamino)-2-methylphenyl-4-azaphthalide, 3-(4-diethylamino phenyl)-3-(1-ethyl-2-methylindol-3-yl) phthalide, 3-(2-methyl-1-n-octylindol-3-yl)-3-(4-diethylamino-2-ethoxyphenyl)-4-azaphthalide, 3-(N-ethyl-N-isopentylamino)-6-methyl-7-anilinofluoran, 3-diethylamino-6-methyl-7-anilinofluoran, 3-diethylamino-6-methyl-7-(o,p-dimethyl anilino) fluoran, 3-(N-ethyl-N-p-toluidino)-6-methyl-7-anilinofluoran, 3-pyrrolidino-6-methyl-7-anilinofluoran, 3-dibutylamino-6-methyl-7-anilinofluoran, 3-(N-cyclohexyl-N-methylamino)-6-methyl-7-anilinofluoran, 3-diethylamino-7-(o-chloroanilino) fluoran, 3-diethylamino-7-(m-trifluoro methylanilino) fluoran, 3-di(n-pentyl) amino-6-methyl-7-anilinofluoran, 3-[N-(3-ethoxypropyl)-N-ethylamino] 6-methyl-7-anilinofluoran, 3-(N-n-hexyl-N-ethylamino)-7-(o-chloroanilino) fluoran, 3-(N-ethyl-N-2-tetrahydrofurfurylamino)-6-methyl-7-anilinofluoran, 2,2-bis{4-[6'-(N-cyclohexyl-N-methylamino)-3'-methylspiro[phthalide-3,9'-xanthen]-2'-ylamino]phenyl}propane, and 3-dibutylamino-7-(o-chloroanilino)fluoran, 3,6-dimethoxyfluorane, 3-pyrrolidino-6-chlorofluoran, 3-diethylamino-6-methyl-7-chlorofluoran, 3-diethylamino-7-chlorofluoran, 3-diethylamino-7,8-dibenzofluoran, 3-diethylamino-6,7-dimethyl fluoran, 3-(N-methyl-p-toluidino)-7-methyl fluoran, 3-(N-methyl-N-isoamylamino)-7,8-benzofluoran, 3,3'-bis(1-n-amyl-2-methylindol-3-yl) phthalide, 3-(N-methyl-N-isoamylamino)-7-phenoxyfluoran, 3,3'-bis(1-n-butyl-2-methylindol-3-yl) phthalide, 3,3'-bis(1-ethyl-2-methylindol-3-yl) phthalide, 3,3'-bis(p-dimethylamino phenyl) phthalide, 3-(N-ethyl-N-p-tolylamino)-7-(N-phenyl-N-methylamino) fluoran, 3-diethylamino-7-anilinofluoran, 3-diethylamino-7-benzylaminofluoran, 3-pyrrolidino-7-dibenzylaminofluoran, and the like. The present invention is not limited thereto and two or more types may be used together.

In the heat-sensitive recording material according to one embodiment of the present invention, a sensitizer conventionally known in the related art as a sensitizer can be used together.

Examples thereof include fatty acid amides such as stearic acid amide, bisstearic acid amide, and palmitic acid amide, calcium such as p-toluenesulfonamide, stearic acid, behenic acid, and palmitic acid, fatty acid metal salts such as a calcium, zinc or aluminum salt, p-benzylbiphenyl, diphenylsulfone, benzyl benzyloxybenzoate, 2-benzyloxynaphthalene, 1,2-bis(p-tolyloxy) ethane, 1,2-bis(phenoxy) ethane, 1,2-bis(3-methylphenoxy) ethane, 1,3-bis(phenoxy) propane, dibenzyl oxalate, p-methylbenzyl oxalate, m-terphenyl, 1-hydroxy-2-naphthoic acid, and the like.

Furthermore, it is possible to use the heat-sensitive recording material according to one embodiment of the present invention together with a storage stabilizer known in the related art.

Examples thereof include a hindered phenol compound such as 2,2'-methylene bis(4-methyl-6-tert-butylphenol), 2,2'-methylene bis(4-ethyl-6-tert-butylphenol), 2,2'-ethylidene bis(4,6-di-tert-butylphenol), 4,4'-thio bis(2-methyl-6-tert-butylphenol), 4,4'-butylidene bis(6-tert-butyl m-cresol), 1,1,3-tris(2-methyl-4-hydroxy-5-tert-butylphenyl) butane, 1,1,3-tris(2-methyl-4-hydroxy-5-cyclo hexyl phenyl) butane, 4,4'-bis[(4-methyl-3-phenoxycarbonylamino phenyl)ureido] diphenylsulfone, tris(2,6-dimethyl-4-tert-butyl-3-hydroxybenzyl) isocyanurate, 4,4'-thio bis(3-methylphenol), 4,4'-dihydroxy-3,3',5,5'-tetrabromodiphenylsulfone, 4,4'-dihydroxy 3,3',5,5'-tetramethyldiphenylsulfone, 2,2-bis(4-hydroxy-3,5-dibromophenyl) propane, 2,2-bis(4-hydroxy-3,5-dichlorophenyl) propane, and 2,2-bis(4-hydroxy-3,5-dimethyl phenyl) propane, epoxy compounds such as 1,4-diglycidyloxy benzene, 4,4'-diglycidyloxy diphenylsulfone, 4-benzyloxy-4'-(2-methylglycyloxy) diphenylsulfone, glycidyl terephthalate, bisphenol A type epoxy resin, cresol novolak type epoxy resin, and phenol novolac type epoxy resin, N,N'-di-2-naphthyl-p-phenylene diamine, a sodium salt or a polyvalent metal salt of 2,2'-methylene bis(4,6-di-tert-butylphenyl) phosphate, bis(4-ethyleneimine carbonylamino phenyl) methane, 4,4'-bis[(4-methyl-3-phenoxycarbonylamino phenyl) ureido] diphenylsulfone, and a diphenylsulfone cross-linking type compound represented by the following General Formula (2). These storage stabilizers contribute to the improvement of the storage stability of the printed portion of the heat-sensitive recording material.

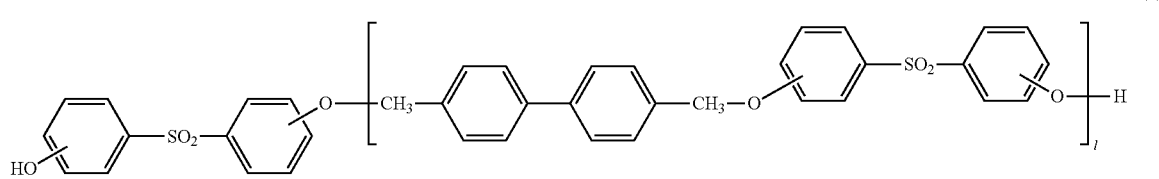

(2)

In the formula, 1 represents an integer of 1 to 6.

Among these storage stabilizers, it is preferable to contain at least one type selected from 1,1,3-tris(2-methyl-4-hydroxy-5-tert-butylphenyl) butane, 1,1,3-tris(2-methyl-4-hydroxy-5-cyclo hexyl phenyl) butane, 4,4'-bis[(4-methyl-3-phenoxycarbonylamino phenyl) ureido] diphenylsulfone, and a diphenylsulfone cross-linking type compound represented by the aforementioned General Formula (2). The water resistance in the printed portion of the heat-sensitive recording material is particularly improved by including these storage stabilizers.

The amount of the storage stabilizer preferably ranges from 2.5 to 100 parts by mass, and more preferably ranges from 5 to 50 parts by mass, with respect to 100 parts by mass of the developer.

In addition, examples of auxiliary agents include a dispersant such as sodium dioctyl succinate, sodium dodecylbenzene sulfonate, sodium lauryl alcohol sulfate ester, and fatty acid metal salts, waxes such as zinc stearate, calcium stearate, polyethylene wax, carnauba wax, paraffin wax, and ester wax, hydrazide compounds such as adipic acid dihydrazide, waterproof agents such as glyoxal, boric acid, dialdehyde starch, methylol urea, glyoxylate, and epoxy-based compounds, defoaming agents, coloring dyes, fluorescent dyes, pigments, and the like.

In the heat-sensitive recording material according to one embodiment of the present invention, examples of the binder used for the heat-sensitive recording layer include fully saponified polyvinyl alcohols having a degree of polymerization ranging from 200 to 1900, partially saponified polyvinyl alcohols, carboxy-modified polyvinyl alcohols, diacetone-modified polyvinyl alcohols, acetoacetyl-modified polyvinyl alcohols, amide-modified polyvinyl alcohols, sulfonic acid-modified polyvinyl alcohols, butyral-modified polyvinyl alcohols, cellulose derivatives such as hydroxyethyl cellulose, methyl cellulose, carboxymethyl cellulose, styrene-maleic anhydride copolymer, styrene-butadiene copolymer and ethyl cellulose, and acetyl cellulose, polyvinyl acetate, polyacrylamide, polyacrylic acid ester, polyvinyl butyral polystyrol and a copolymer thereof, a polyamide resin, a silicone resin, a petroleum resin, a terpene resin, a ketone resin, a chromane resin, and the like. These binders can be used alone or in combination of two or more types. The binders may be used by being dissolved in a solvent, or may be used in a state of being emulsified or dispersed as a paste in water or another medium.

Examples of the pigment blended in the heat-sensitive recording layer include inorganic or organic pigments such as silica, calcium carbonate, kaolin, calcined kaolin, diatomaceous earth, talc, titanium oxide, zinc oxide, aluminum hydroxide, polystyrene resin, urea-formalin resin, styrene-methacrylic acid copolymers, styrene-butadiene copolymers, hollow plastic pigments, and the like.

In the heat-sensitive recording material according to one embodiment of the present invention, the types and amounts of basic dyes, developers, sensitizers, binders, pigments, and other additives used in the heat-sensitive recording layer are appropriately determined according to the quality performances required in the heat-sensitive recording layer.

In the heat-sensitive recording layer of the heat-sensitive recording material according to one embodiment of the present invention, the amount of the N-substituted amino acid derivative represented by the aforementioned General Formula (1) as a developer preferably ranges from 0.3 to 5 parts by mass, and more preferably ranges from 0.4 to 3 parts by mass, with respect to 1 part by mass of the basic dye of the heat-sensitive recording layer, from the point of view of coloring density.

Furthermore, the sensitizer is suitably in an amount of 0.2 to 4 parts by mass with respect to 1 part of the leuco dye, and the binder is suitably in an amount of 5 to 50% by mass of the total solid content. As the supporting body, paper, recycled paper, synthetic paper, plastic film, non-woven fabric, metal foil, and the like can be used. In addition, composite sheets combining these materials can also be used.

In addition, for the purpose of enhancing storage stability, an overcoating layer formed of a polymer substance containing an organic pigment may be provided. Furthermore, for the purpose of preventing adhesion of dust to the thermal head, improving printing image quality, and improving sensitivity, an undercoating layer containing an organic pigment, an inorganic pigment, hollow fine particles, and the like may be provided.

In the heat-sensitive recording material according to one embodiment of the present invention, the basic dye, developer, sensitizer, and storage stabilizer as necessary, and the like, which are used in the heat-sensitive recording layer, are used after being finely dispersed in, for example, water as a dispersion medium using a stirring and pulverizing machine such as a ball mill, an attritor, or a sand mill so that the average particle diameter becomes 2 μm or less.

A heat-sensitive recording layer coating is prepared by mixing and stirring a pigment, a binder, an auxiliary agent and the like, as necessary, into the dispersion liquid finely dispersed as described above.

The heat-sensitive recording layer coating obtained as described above is applied on a supporting body such that the coating amount after drying is approximately 1.5 to 12 g/m$^2$, and more preferably about 3 to 7 g/m$^2$, and dried to form a heat-sensitive recording layer.

EXAMPLES

Hereinafter, the present invention will be specifically described with reference to Examples and Comparative Examples, but the present invention is not limited thereto. Here, in the examples, "parts" and "%" represent "parts by mass" and "% by mass".

Synthesis examples of the N-substituted amino acid derivatives used in the examples are given below.

Synthesis Example 1:
N-(m-tolylaminocarbonyl)-phenylalanine 16.5 g of L-phenylalanine and 50 g of water were placed in a four-necked flask equipped with a thermometer, a dropping funnel, and a stirrer, then the internal temperature was adjusted to 15° C., 50 g of an 8% aqueous solution of sodium hydroxide was added thereto, and the L-phenylalanine was dissolved. While maintaining the internal temperature at 15° C., 13.3 g of m-tolyl isocyanate dissolved in ethyl acetate was added dropwise thereto and the mixture was stirred for 5 hours. Ethyl acetate was added to the reaction solution, the mixture was neutralized with diluted hydrochloric acid, and the product was extracted with ethyl acetate. The ethyl acetate of the extract was concentrated, then toluene was added to the concentrated residue to cause crystallization. The crystals were separated by filtration and dried to obtain N-(m-tolylaminocarbonyl)-phenylalanine as a white crystal. The melting point was 151° C.

Synthesis Example 2:
N-(m-tolylaminocarbonyl)-methionine

N-(m-tolylaminocarbonyl)-methionine as a white crystal was obtained by the same operation as in Synthesis Example 1 except that 14.9 g of L-methionine was used in place of the 16.5 g of L-phenylalanine of Synthesis Example 1. The melting point was 142° C.

Synthesis Example 3:
N-(m-tolylaminocarbonyl)-valine

N-(m-tolylaminocarbonyl)-valine as a white crystal was obtained by the same operation as in Synthesis Example 1 except that 11.7 g of L-valine was used in place of the 16.5 g of L-phenylalanine of Synthesis Example 1. The melting point was 169° C.

Synthesis Example 4:
N-(m-tolylaminocarbonyl)-cysteine-S-benzyl

N-(m-tolylaminocarbonyl)-cysteine-S-benzyl as a white crystal was obtained by the same operation as in Synthesis Example 1 except that 21.1 g of L-cysteine-S-benzyl was used in place of the 16.5 g of L-phenylalanine of Synthesis Example 1. The melting point was 164° C.

Synthesis Example 5:
N-(m-tolylaminocarbonyl)-tyrosine

N-(m-tolylaminosulfonyl)-tyrosine as a white crystal was obtained by the same operation as in Synthesis Example 1 except that 18.1 g of L-tyrosine was used in place of the 16.5 g of L-phenylalanine of Synthesis Example 1. The melting point was 161° C.

Synthesis Example 6:
N-phenylaminothiocarbonyl-glycylglycine 13.2 g of glycylglycine, 50 g of water, and 50 g of THF were charged into the same apparatus as in Synthesis Example 1, and 50 g of an 8% aqueous solution of sodium hydroxide was added to dissolve the glycylglycine. While maintaining the internal temperature at 20 to 25° C., 13.5 g of phenyl isothiocyanate was added dropwise thereto and the mixture was stirred for 5 hours.

The same reaction procedure as in Synthesis Example 1 was carried out to obtain N-phenylaminothiocarbonyl-glycylglycine as a white crystal. The melting point was 157° C.

Synthesis Example 7: N-(p-toluenesulfonylaminocarbonyl)-phenylalanine-methyl ester 21.5 g of L-phenylalanine-methyl ester hydrochloride and 120 g of ethyl acetate were charged into a four-necked flask provided with a thermometer, a dropping funnel, and a stirrer, and 10.1 g of triethylamine was added dropwise thereto while maintaining the internal temperature at 10° C. While maintaining the internal temperature at 8 to 10° C., 19.7 g of p-toluenesulfonyl isocyanate was added dropwise thereto and stirring was continued for 5 hours. After completion of the reaction, a small amount of acetic acid was added to the reaction solution, and water was added to wash and separate the organic layer. Toluene was added to the residue obtained by concentrating the organic layer under reduced pressure to precipitate crystals, and white crystals of N-(p-toluenesulfonylaminocarbonyl)-phenylalanine-methyl ester were obtained by filtration. The melting point was 162° C.

Synthesis Example 8:
N-(p-toluenesulfonyl)-β-alanine 8.9 g of β-alanine, 30 g of water, and an 8%0/aqueous solution of sodium hydroxide were charged into a four-necked flask provided with a thermometer, a dropping funnel, and a stirrer, and cooled to an internal temperature of 10° C. 30 g of a THF solution in which 19.1 g of p-toluenesulfonyl chloride was dissolved and 50 g of an 8% sodium hydroxide were each divided into four fractions, and the respective fractions were alternately added dropwise to the flask to cause a reaction. After stirring for 4 hours, the mixture was acidified with diluted hydrochloric acid. The reaction solution was subjected to a reaction treatment in the same manner as in Synthesis Example 1 to obtain N-(p-toluenesulfonyl)-β-alanine as a white crystal. The melting point was 125° C.

A heat-sensitive recording material was prepared by the following operation.

[Preparation of Coating for Undercoating]

100 parts of plastic hollow particles (trade name: ROPAQUE SN-1055: hollow ratio: 55%, solid content 26.5%), 100 parts of calcined kaolin in the form of a 50% dispersion liquid, 25 parts of styrene-butadiene-based latex (trade name: L-1571, solid content 48%), 50 parts of a 10% aqueous solution of oxidized starch, and 20 parts of water were mixed to prepare a coating for an undercoat.

Example 1

[Preparation of Coating for Use in Heat-Sensitive Recording]

| Liquid A (Preparation of Dye Dispersion Liquid) | |
| --- | --- |
| 3-(N,N-dibutylamino)-6-methyl-7-anilinofluoran | 10 parts |
| 10% aqueous solution of polyvinyl alcohol | 10 parts |
| Water | 16.7 parts |

| Liquid B (Preparation of Developer Dispersion Liquid) | |
| --- | --- |
| N-(m-tolylaminocarbonyl)-phenylalanine (Developer 1) | 20 parts |
| 10% aqueous solution of polyvinyl alcohol | 20 parts |
| Water | 33.3 parts |

| Liquid C (Preparation of Sensitizer Dispersion Liquid) | |
| --- | --- |
| 1,2-bis(m-tolyloxy) ethane | 15 parts |
| 10% aqueous solution of polyvinyl alcohol | 15 parts |
| Water | 25 parts |

Dispersion liquids of the aforementioned Liquid A, Liquid B, and Liquid C were pulverized by a sand grinder until the average particle diameter became 1 µm or less, and the dispersion liquids were mixed at the following ratio to prepare a coating liquid.

| | |
| --- | --- |
| Liquid A (dye agent dispersion liquid) | 36.7 parts |
| Liquid B (developer dispersion liquid) | 73.3 parts |
| Liquid C (sensitizer dispersion liquid) | 55.0 parts |

Components formed from 20 parts of aluminum hydroxide (trade name: Higilite H-42), 10 parts of amorphous silica (trade name: Mizukasil P-605), 20 parts of a 10% lysate of oxidized starch, 15 parts of zinc stearate dispersion liquid: (trade name: Hydrin Z-8-36), and 20 parts of water were mixed to prepare a coating for use in heat-sensitive recording.

[Preparation of Heat-Sensitive Recording Material]

A coating for use in an undercoating was applied and dried on high quality paper (acidic paper) having a basis weight of 53 g as a supporting body such that the mass per area after drying was 6 g/m². Subsequently, a heat-sensitive coating was applied thereon and dried such that the mass per area was 3.5 g/m² after drying.

This sheet was treated with a supercalender such that the smoothness (JIS P 8155: 2010) was 900 to 1200 s to prepare a heat-sensitive recording material.

[Various Tests]

1. Heat-Sensitive Recording Test (Color Development Test)

The heat-sensitive recording material prepared in this manner was subjected to an applied energy of 0.38 mJ/dot using a heat-sensitive recording paper printing tester (TH-PMD manufactured by Okura Electric Co. Ltd.). The print density of the recorded portion was measured with a Macbeth reflection densitometer RD-914.

2. Heat Resistance Test

The heat-sensitive recording material recorded in the heat-sensitive recording test was left for 24 hours in a constant temperature environment at a test temperature of 60° C. and then the image density of the printed portion of the test piece and the density of the unprinted portion were measured with a Macbeth reflection densitometer.

3. Moisture Resistance Test

The heat-sensitive recording material recorded by the heat-sensitive recording property test was left for 24 hours in an environment of a test temperature of 40° C. and 90% RH, and then the image density of the printed portion of the test piece and the density of the unprinted portion were measured with a Macbeth reflection densitometer.

4. Oil Resistance Test

The heat-sensitive recording material recorded in the heat-sensitive recording test was immersed in salad oil for 1 minute, oil of the test piece was wiped off, and the image density was measured with a Macbeth reflection densitometer.

The various test results of the heat-sensitive recording material according to this example are as shown in Table 1.

Example 2

The same operations as in Example 1 were carried out except that the N-(m-tolylaminocarbonyl)-phenylalanine (Developer 1) in Liquid B of Example 1 was replaced with N-p-toluenesulfonyl)-phenylalanine (Developer 2).

The various test results of the heat-sensitive recording material according to this example are as shown in Table 1.

Example 3

The same operations as in Example 1 were carried out except that the N-(m-tolylaminocarbonyl)-phenylalanine (Developer 1) in Liquid B of Example 1 was replaced with N-(benzyloxycarbonyl)-valine (Developer 3).

The various test results of the heat-sensitive recording material according to this example are as shown in Table 1.

Example 4

The same operations as in Example 1 were carried out except that the N-(m-tolylaminocarbonyl)-phenylalanine (Developer 1) in Liquid B of Example 1 was replaced with N-(m-tolylaminocarbonyl)-methionine (Developer 4).

The various test results of the heat-sensitive recording material according to this example are as shown in Table 1.

Example 5

The same operations as in Example 1 were carried out except that the N-(m-tolylaminocarbonyl)-phenylalanine (Developer 1) in B of Example 1 was replaced with N-(m-tolylaminocarbonyl)-tyrosine (Developer 5).

The various test results of the heat-sensitive recording material according to this example are as shown in Table 1.

Example 6

The same operations as in Example 1 were carried out except that the N-(m-tolylaminocarbonyl)-phenylalanine (Developer 1) in Liquid B of Example 1 was replaced with N-(m-tolylaminocarbonyl)-phenyl glycine (Developer 6). The various test results of the heat-sensitive recording material according to this example are as shown in Table 1.

Example 7

The same operations as in Example 1 were carried out except that the N-(m-tolylaminocarbonyl)-phenylalanine (Developer 1) in Liquid B of Example 1 was replaced with N-(m-tolylaminocarbonyl)-valine (Developer 7). The various test results of the heat-sensitive recording material according to this example are as shown in Table 1.

Example 8

The same operations as in Example 1 were carried out except that the N-(m-tolylaminocarbonyl)-phenylalanine (Developer 1) in Liquid B of Example 1 was replaced with N-(m-tolylaminocarbonyl)-cysteine-S-benzyl (Developer 8). The various test results of the heat-sensitive recording material according to this example are as shown in Table 1.

Example 9

The same operations as in Example 1 were carried out except that the N-(m-tolylaminocarbonyl)-phenylalanine (Developer 1) in Liquid B of Example 1 was replaced with N-(m-tolylaminocarbonyl)-β-alanine (Developer 9). The various test results of the heat-sensitive recording material according to this example are as shown in Table 1.

Example 10

The same operations as in Example 1 were carried out except that the N-(m-tolylaminocarbonyl)-phenylalanine (Developer 1) in Liquid B of Example 1 was replaced with N-phenylaminothiocarbonyl glycylglycine (Developer 10). The various test results of the heat-sensitive recording material according to this example are as shown in Table 1.

Example 11

The same operations as in Example 1 were carried out except that the N-(m-tolylaminocarbonyl)-phenylalanine (Developer 1) in Liquid B of Example 1 was replaced with N-(p-toluenesulfonylaminocarbonyl)-phenylalanine-methyl ester (Developer 11). The various test results of the heat-sensitive recording material according to this example are as shown in Table 1.

Example 12

The same operations as in Example 1 were carried out except that the N-(m-tolylaminocarbonyl)-phenylalanine (Developer 1) in Liquid B of Example 1 was replaced with N-(p-toluenesulfonyl)-β-alanine (Developer 12). The various test results of the heat-sensitive recording material according to this example are as shown in Table 1.

Example 13

The same operations as in Example 1 were carried out except that the N-(m-tolylaminocarbonyl)-phenylalanine (Developer 1) in Liquid B of Example 1 was replaced with N-(p-tolylaminocarbonyl)-methionine (Developer 13). The various test results of the heat-sensitive recording material according to this example are as shown in Table 1.

Example 14

The same operations as in Example 1 were carried out except that the N-(m-tolylaminocarbonyl)-phenylalanine (Developer 1) in Liquid B of Example 1 was replaced with N-(phenylaminocarbonyl)-methionine (Developer 14). The various test results of the heat-sensitive recording material according to this example are as shown in Table 1.

Comparative Example 1

The same operations as in Example 1 were carried out except that the N-(m-tolylaminocarbonyl)-phenylalanine (Developer 1) in Liquid B of Example 1 was replaced with N-acetyl-phenylalanine (Developer 15). The various test results of the heat-sensitive recording material according to this comparative example are as shown in Table 1.

Comparative Example 2

The same operations as in Example 1 were carried out except that the N-(m-tolylaminocarbonyl)-phenylalanine (Developer 1) in Liquid B of Example 1 was replaced with N-benzoyl-valine (Developer 16). The various test results of the heat-sensitive recording material according to this comparative example are as shown in Table 1.

Comparative Example 3

The same operations as in Example 1 were carried out except that the N-(m-tolylaminocarbonyl)-phenylalanine (Developer 1) in Liquid B of Example 1 was replaced with N-benzoyl-β-alanine (Developer 17). The various test results of the heat-sensitive recording material according to this comparative example are as shown in Table 1.

Reference Example 1

The same operations as in Example 1 were carried out except that the N-(m-tolylaminocarbonyl)-phenylalanine (Developer 1) in Liquid B of Example 1 was replaced with bisphenol A (Developer 18). The various test results of the heat-sensitive recording material according to this reference example are as shown in Table 1.

Reference Example 2

The same operations as in Example 1 were carried out except that the N-(m-tolylaminocarbonyl)-phenylalanine (Developer 1) in Liquid B of Example 1 was replaced with 4,4'-bisphenol S (Developer 19). The various test results of the heat-sensitive recording material according to this reference example are as show n in Table 1.

TABLE 1

| | Developer | | Coloring density | Moisture resistance | Heat resistance | Oil resistance |
|---|---|---|---|---|---|---|
| Example 1 | Developer 1 | Unprinted portion | 0.05 | 0.05 | 0.06 | 0.07 |
| | | Printed portion | 1.25 | 1.20 | 1.25 | 0.85 |
| Example 2 | Developer 2 | Unprinted portion | 0.05 | 0.05 | 0.12 | 0.07 |
| | | Printed portion | 1.28 | 1.16 | 1.23 | 0.80 |
| Example 3 | Developer 3 | Unprinted portion | 0.05 | 0.05 | 0.06 | 0.07 |
| | | Printed portion | 1.21 | 1.15 | 1.15 | 0.40 |

TABLE 1-continued

| | Developer | | Coloring density | Moisture resistance | Heat resistance | Oil resistance |
|---|---|---|---|---|---|---|
| Example 4 | Developer 4 | Unprinted portion | 0.05 | 0.05 | 0.06 | 0.07 |
| | | Printed portion | 1.33 | 1.21 | 1.32 | 0.81 |
| Example 5 | Developer 5 | Unprinted portion | 0.05 | 0.06 | 0.06 | 0.07 |
| | | Printed portion | 1.20 | 1.17 | 1.16 | 1.07 |
| Example 6 | Developer 6 | Unprinted portion | 0.05 | 0.06 | 0.06 | 0.07 |
| | | Printed portion | 1.31 | 1.20 | 1.25 | 1.05 |
| Example 7 | Developer 7 | Unprinted portion | 0.05 | 0.05 | 0.06 | 0.06 |
| | | Printed portion | 1.32 | 1.23 | 1.20 | 1.06 |
| Example 8 | Developer 8 | Unprinted portion | 0.05 | 0.05 | 0.05 | 0.08 |
| | | Printed portion | 1.31 | 1.18 | 1.21 | 0.71 |
| Example 9 | Developer 9 | Unprinted portion | 0.05 | 0.06 | 0.06 | 0.07 |
| | | Printed portion | 1.15 | 0.75 | 0.81 | 0.62 |
| Example 10 | Developer 10 | Unprinted portion | 0.05 | 0.06 | 0.06 | 0.07 |
| | | Printed portion | 1.05 | 0.81 | 0.75 | 0.52 |
| Example 11 | Developer 11 | Unprinted portion | 0.05 | 0.06 | 0.05 | 0.08 |
| | | Printed portion | 1.10 | 0.77 | 0.70 | 0.39 |
| Example 12 | Developer 12 | Unprinted portion | 0.05 | 0.06 | 0.12 | 0.08 |
| | | Printed portion | 1.10 | 0.72 | 0.85 | 0.45 |
| Example 13 | Developer 13 | Unprinted portion | 0.05 | 0.05 | 0.06 | 0.07 |
| | | Printed portion | 1.28 | 1.20 | 1.24 | 0.82 |
| Example 14 | Developer 14 | Unprinted portion | 0.05 | 0.05 | 0.06 | 0.07 |
| | | Printed portion | 1.30 | 1.21 | 1.24 | 0.86 |
| Comparative Example 1 | Developer 15 | Unprinted portion | 0.05 | 0.05 | 0.05 | 0.08 |
| | | Printed portion | 0.78 | 0.40 | 0.42 | 0.22 |
| Comparative Example 2 | Developer 16 | Unprinted portion | 0.05 | 0.05 | 0.05 | 0.06 |
| | | Printed portion | 0.47 | 0.31 | 0.34 | 0.12 |
| Comparative Example 3 | Developer 17 | Unprinted portion | 0.05 | 0.05 | 0.05 | 0.06 |
| | | Printed portion | 0.49 | 0.33 | 0.34 | 0.28 |
| Reference Example 1 | Developer 18 | Unprinted portion | 0.05 | 0.06 | 0.07 | 0.07 |
| | | Printed portion | 1.35 | 1.32 | 1.18 | 0.27 |
| Reference Example 2 | Developer 19 | Unprinted portion | 0.05 | 0.05 | 0.06 | 0.08 |
| | | Printed portion | 1.25 | 1.24 | 1.20 | 0.68 |

As is clear from the Examples and Table 1, the heat-sensitive recording materials prepared from amino acid derivatives exhibited good coloring density with high whiteness, and in particular, in the case of Z being an OH group, X being —NHCO—, and in addition, the N-substituted amino acid derivative being N-(m-tolylaminocarbonyl)-phenylalanine, N-(m-tolylaminocarbonyl)-methionine, N-(m-tolylaminocarbonyl)-valine, N-(m-tolylaminocarbonyl)-phenylglycine, and N-(m-tolylaminocarbonyl)-tyrosine, the heat-sensitive recording materials also had good storage stability in terms of the heat resistance, moisture resistance, and oil resistance of the printed portions and unprinted portions.

Example 15

[Preparation of Coating for Use in Heat-Sensitive Recording]

| Liquid A (Preparation of Dye Dispersion Liquid) | |
|---|---|
| 3-(N,N-dibutylamino)-6-methyl-7-anilinofluoran | 10 parts |
| 10% aqueous solution of polyvinyl alcohol | 10 parts |
| Water | 16.7 parts |

| Liquid B (Preparation of Developer Dispersion Liquid) | |
|---|---|
| N-(m-tolylaminocarbonyl)-methionine (Developer 4) | 20 parts |
| 10% aqueous solution of polyvinyl alcohol | 20 parts |
| Water | 33.3 parts |

| Liquid C (Preparation of Sensitizer Dispersion Liquid) | |
|---|---|
| 1,2-bis(m-tolyloxy) ethane | 15 parts |
| 10% aqueous solution of polyvinyl alcohol | 15 parts |
| Water | 25 parts |

| Liquid D (Preparation of Storage Stabilizer Liquid) | |
|---|---|
| 1,1,3-tris(2-methyl-4-hydroxy-5-cyclohexylphenyl)butane | 5 parts |
| 10% aqueous solution of polyvinyl alcohol | 5 parts |
| Water | 8.33 parts |

Dispersion liquids of the aforementioned Liquid A, Liquid B, Liquid C, and Liquid D were pulverized by a sand grinder until the average particle diameter became 1 μm or less, and the dispersion liquids were mixed at the following ratio to prepare a coating liquid.

| Liquid A (dye agent dispersion liquid) | 36.7 parts |
|---|---|
| Liquid B (developer dispersion liquid) | 73.3 parts |
| Liquid C (sensitizer dispersion liquid) | 55.0 parts |
| Liquid D (storage stabilizer liquid) | 18.33 parts |

Components formed from 20 parts of aluminum hydroxide (trade name: Higilite H-42), 10 parts of amorphous silica (trade name: Mizukasil P-605), 20 parts of a 10% lysate of oxidized starch, 15 parts of a zinc stearate dispersion liquid (trade name: Hydrin Z-8-36), and 20 parts of water were mixed to prepare a coating for use in heat-sensitive recording.

[Preparation of Heat-Sensitive Recording Material]

A coating for an undercoating was applied and dried on high quality paper (acidic paper) having a basis weight of 53 g as a supporting body such that the mass per area after drying was 6 g/m². Subsequently, the heat-sensitive coating was applied thereon and dried such that the mass per area was 3.5 g/m² after drying.

This sheet was treated with a supercalender such that the smoothness (JIS P 8155: 2010) was 900 to 1200 s to prepare a heat-sensitive recording material.

[Various Tests]

With respect to the prepared heat-sensitive recording materials, 1. Heat-Sensitive Recording Test (Color Development Test), 2. Heat Resistance Test, and 3. Moisture Resistance Test were conducted in the same manner as in the case of Example 1. 4. Oil Resistance Test, 5. Water Resistance Test, and 6. Plasticizer Resistance Test were carried out using the following method.

4. Oil Resistance Test

The heat-sensitive recording paper recorded in the heat-sensitive recording test was immersed in a salad oil for 10 minutes, then the oil of the test piece was wiped off and the image density was measured with a Macbeth reflection densitometer.

5. Water Resistance Test

The heat-sensitive recording paper recorded in the heat-sensitive recording test was immersed in water for 24 hours, then the test piece was air-dried, and the image density and the unprinted portion density were measured with a Macbeth reflection densitometer.

6. Plasticizer Resistance Test

A wrap film (trade name: HIGH WRAP KMA manufactured by Mitsui Chemicals, Inc.) was wound three revolutions around a polycarbonate pipe (48 mm 4), the heat-sensitive recording paper recorded in the heat-sensitive recording test was placed thereon, and the wrap film was further wound three revolutions therearound and left to stand for 24 hours in an environment of 20° C. and 65% RH. Subsequently, the image density and the unprinted portion density were measured with a Macbeth reflection densitometer.

The various test results of the heat-sensitive recording material according to this example are as shown in Table 2.

Example 16

The same operations as in Example 15 were carried out except that the N-(m-tolylaminocarbonyl)-methionine (Developer 4) in Liquid B of Example 15 was replaced with N-(m-tolylaminocarbonyl)-phenylalanine (Developer 1).

The various test results of the heat-sensitive recording material according to this example are as shown in Table 2.

Example 17

The same operations as in Example 15 were carried out except that the N-(m-tolylaminocarbonyl)-methionine (Developer 4) in Liquid B of Example 15 was replaced with N-(phenylaminocarbonyl)-methionine (Developer 14).

The various test results of the heat-sensitive recording material according to this example are as shown in Table 2.

Example 18

The same operations as in Example 15 were carried out except that the N-(m-tolylaminocarbonyl)-methionine (Developer 4) of Liquid B of Example 15 was replaced with N-(p-tolylaminocarbonyl)-methionine (Developer 13).

The various test results of the heat-sensitive recording material according to this example are as shown in Table 2.

Example 19

The same operations as in Example 15 were carried out except that the N-(m-tolylaminocarbonyl)-methionine (Developer 4) of Liquid B of Example 15 was replaced with N-m-tolylaminocarbonyl)-valine (Developer 7).

The various test results of the heat-sensitive recording material according to this example are as shown in Table 2.

Example 20

The same operations as in Example 15 were carried out except that the N-(m-tolylaminocarbonyl)-methionine (Developer 4) of Liquid B of Example 15 was replaced with N-(m-tolylaminocarbonyl)-phenylglycine (Developer 6).

The various test results of the heat-sensitive recording material according to this example are as shown in Table 2.

Example 21

The same operations as in Example 15 were carried out except that the N-(m-tolylaminocarbonyl)-methionine (Developer 4) of Liquid B of Example 15 was replaced with N-(m-tolylaminocarbonyl)-tyrosine (Developer 5).

The various test results of the heat-sensitive recording material according to this example are as shown in Table 2.

Example 22

The same operations as in Example 15 were carried out except that the 1,1,3-tris(2-methyl-4-hydroxy-5-cyclohexylphenyl)butane in Liquid D of Example 15 was replaced with 1,1,3-tris(2-methyl-4-hydroxy-5-tert-butylphenyl)butane.

The various test results of the heat-sensitive recording material according to this example are as shown in Table 2.

Example 23

The same operations as in Example 15 were carried out except that the 1,1,3-tris(2-methyl-4-hydroxy-5-cyclohexylphenyl)butane in Liquid D of Example 15 was replaced with a diphenylsulfone cross-linking type compound (trade name: D-90, manufactured by Nippon Soda Co. Ltd, a mixture of compounds in which 1 is 1 to 6 in Formula (2)).

The various test results of the heat-sensitive recording material according to this example are as shown in Table 2.

Example 24

The same operations as in Example 15 were carried out except that the 1,1,3-tris(2-methyl-4-hydroxy-5-cyclohexylphenyl)butane in Liquid D of Example 1 was replaced with 4,4'-bis[(4-methyl-3-phenoxycarbonylaminophenyl) ureido] phenylsulfone.

The various test results of the heat-sensitive recording material according to this example are as shown in Table 2.

Example 25

The same operations as in Example 15 were carried out except that the amount of 1,1,3-tris(2-methyl-4-hydroxy-5-cyclohexylphenyl)butane in Liquid D of Example 1 was replaced with 9.165 parts. The various test results of the heat-sensitive recording material according to this example are as shown in Table 2.

Example 26

The same operations as in Example 15 were carried out except that the amount of 1,1,3-tris(2-methyl-4-hydroxy-5-cyclohexylphenyl)butane in Liquid D of Example 1 was replaced with 36.67 parts.

The various test results of the heat-sensitive recording material according to this example are as shown in Table 2.

The various test results of the heat-sensitive recording material according to this example are as shown in Table 3.

Reference Examples 3 to 9

Reference Examples 1 to 7 (Examples 4, 1, 14, 13, 7, 6, and 5) are the same as Example 15 except that Liquid D was not used in Examples 15 to 21. The various test results of the heat-sensitive recording material according to Reference Examples 3 to 9 (Examples 4, 1, 14, 13, 7, 6, and 5) are as shown in Table 3.

TABLE 2

|  | Developer | Storage Stabilizer |  | Coloring density | Moisture resistance | Heat resistance | Water resistance | Oil resistance | Plasticizer resistance |
|---|---|---|---|---|---|---|---|---|---|
| Example 15 | Developer 4 | 1,1,3-tris(2-methyl-4-hydroxy-5-cyclohexylphenyl)butane | Unprinted portion Printed portion | 0.05 1.32 | 0.05 1.27 | 0.06 1.32 | 0.05 0.83 | 0.07 0.80 | 0.05 0.48 |
| Example 16 | Developer 1 | 1,1,3-tris(2-methyl-4-hydroxy-5-cyclohexylphenyl)butane | Unprinted portion Printed portion | 0.05 1.24 | 0.05 1.22 | 0.06 1.24 | 0.05 0.95 | 0.07 0.77 | 0.05 0.45 |
| Example 17 | Developer 14 | 1,1,3-tris(2-methyl-4-hydroxy-5-cyclohexylphenyl)butane | Unprinted portion Printed portion | 0.05 1.30 | 0.05 1.25 | 0.06 1.28 | 0.05 0.84 | 0.07 1.01 | 0.05 0.55 |
| Example 18 | Developer 13 | 1,1,3-tris(2-methyl-4-hydroxy-5-cyclohexylphenyl)butane | Unprinted portion Printed portion | 0.05 1.27 | 0.05 1.22 | 0.06 1.25 | 0.05 0.67 | 0.07 0.77 | 0.05 0.44 |
| Example 19 | Developer 7 | 1,1,3-tris(2-methyl-4-hydroxy-5-cyclohexylphenyl)butane | Unprinted portion Printed portion | 0.05 1.30 | 0.05 1.26 | 0.06 1.25 | 0.05 0.72 | 0.05 0.75 | 0.05 0.44 |
| Example 20 | Developer 6 | 1,1,3-tris(2-methyl-4-hydroxy-5-cyclohexylphenyl)butane | Unprinted portion Printed portion | 0.05 1.29 | 0.06 1.23 | 0.06 1.27 | 0.05 0.77 | 0.07 0.91 | 0.05 0.50 |
| Example 21 | Developer 5 | 1,1,3-tris(2-methyl-4-hydroxy-5-cyclohexylphenyl)butane | Unprinted portion Printed portion | 0.05 1.18 | 0.06 1.17 | 0.06 1.18 | 0.05 0.62 | 0.07 0.88 | 0.05 0.48 |
| Example 22 | Developer 4 | 1,1,3-tris(2-methyl-4-hydroxy-5-tert-butylphenyl)butane | Unprinted portion Printed portion | 0.05 1.30 | 0.05 1.29 | 0.06 1.28 | 0.05 0.92 | 0.05 0.84 | 0.05 0.47 |
| Example 23 | Developer 4 | Diphenylsulfone cross-linking type compound | Unprinted portion Printed portion | 0.05 1.34 | 0.05 1.28 | 0.06 1.30 | 0.05 0.75 | 0.07 1.15 | 0.05 0.58 |
| Example 24 | Developer 4 | 4,4'-bis[(4-methyl-3-phenoxycarbonylaminophenyl)ureido]phenyl sulfone | Unprinted portion Printed portion | 0.05 1.30 | 0.05 1.23 | 0.06 1.27 | 0.05 0.73 | 0.07 1.08 | 0.05 0.48 |
| Example 25 | Developer 4 | 1,1,3-tris(2-methyl-4-hydroxy-5-cyclohexylphenyl)butane | Unprinted portion Printed portion | 0.05 1.32 | 0.05 1.22 | 0.06 1.28 | 0.05 0.50 | 0.07 0.72 | 0.05 0.47 |
| Example 26 | Developer 4 | 1,1,3-tris(2-methyl-4-hydroxy-5-cyclohexylphenyl)butane | Unprinted portion Printed portion | 0.05 1.30 | 0.05 1.27 | 0.06 1.27 | 0.05 0.86 | 0.07 0.85 | 0.05 0.48 |

Example 27

The same operations as in Example 15 were carried out except that the amount of 1,1,3-tris(2-methyl-4-hydroxy-5-cyclohexylphenyl)butane in Liquid D of Example 1 was replaced with 73.34 parts.

The various test results of the heat-sensitive recording material according to this example are as shown in Table 3.

Example 28

The same operations as in Example 15 were carried out except that 1,1,3-tris(2-methyl-4-hydroxy-5-cyclohexylphenyl)butane in Liquid D of Example 15 was replaced with 1,1,3-tris(2-methyl-4-hydroxy-5-cyclohexylphenyl)butane and a diphenylsulfone cross-linking type compound at a mixing ratio of 1:1.

Reference Example 1

Reference Example 1 is the same as Example 15 except that N-(m-tolylaminocarbonyl)-methionine in Liquid B in Example 15 was replaced with bisphenol A (Developer 18). The various test results of the heat-sensitive recording material according to Reference Example 1 are as shown in Table 3.

Reference Example 2

Reference Example 2 is the same as Example 15 except that N-(m-tolylaminocarbonyl)-methionine (Developer 4) in Liquid B of Example 15 was replaced with 4,4'-bisphenol S (Developer 19). The various test results of the heat-sensitive recording material according to Reference Example 2 are as shown in Table 3.

TABLE 3

| | Developer | Storage Stabilizer | | Coloring density | Moisture resistance | Heat resistance | Water resistance | Oil resistance | Plasticizer resistance |
|---|---|---|---|---|---|---|---|---|---|
| Example 27 | Developer 4 | 1,1,3-tris(2-methyl-4-hydroxy-5-cyclohexylphenyl)butane | Unprinted portion | 0.05 | 0.05 | 0.06 | 0.05 | 0.07 | 0.05 |
| | | | Printed portion | 1.25 | 1.24 | 1.23 | 0.85 | 0.84 | 0.46 |
| Example 28 | Developer 4 | 1,1,3-tris(2-methyl-4-hydroxy-5 cyclohexylphenyl)butane/ diphenylsulfone cross-linking type compound | Unprinted portion | 0.05 | 0.05 | 0.06 | 0.05 | 0.07 | 0.05 |
| | | | Printed portion | 1.30 | 1.28 | 1.28 | 0.86 | 0.94 | 0.51 |
| Reference example 3 (Example 4) | Developer 4 | Not used | Unprinted portion | 0.05 | 0.05 | 0.06 | 0.05 | 0.07 | 0.05 |
| | | | Printed portion | 1.33 | 1.21 | 1.32 | 0.38 | 0.70 | 0.49 |
| Reference example 4 (Example 1) | Developer 1 | Not used | Unprinted poition | 0.05 | 0.05 | 0.06 | 0.05 | 0.07 | 0.05 |
| | | | Printed portion | 1.25 | 1.20 | 1.25 | 0.50 | 0.73 | 0.42 |
| Reference example 5 (Example 14) | Developer 14 | Not used | Unprinted poition | 0.05 | 0.05 | 0.06 | 0.06 | 0.07 | 0.05 |
| | | | Printed portion | 1.30 | 1.21 | 1.24 | 0.31 | 0.75 | 0.43 |
| Reference example 6 (Example 13) | Developer 13 | Not used | Unprinted portion | 0.05 | 0.05 | 0.06 | 0.05 | 0.07 | 0.05 |
| | | | Printed portion | 1.28 | 1.20 | 1.24 | 0.25 | 0.70 | 0.40 |
| Reference example 7 (Example 7) | Developer 7 | Not used | Unprinted portion | 0.05 | 0.05 | 0.06 | 0.05 | 0.06 | 0.05 |
| | | | Printed portion | 1.32 | 1.23 | 1.20 | 0.31 | 0.86 | 0.48 |
| Reference example 8 (Example 6) | Developer 6 | Not used | Unprinted portion | 0.05 | 0.06 | 0.06 | 0.05 | 0.07 | 0.05 |
| | | | Printed portion | 1.31 | 1.20 | 1.25 | 0.35 | 0.86 | 0.45 |
| Reference example 9 (Example 5) | Developer 5 | Not used | Unprinted portion | 0.05 | 0.06 | 0.06 | 0.05 | 0.07 | 0.05 |
| | | | Printed portion | 1.20 | 1.17 | 1.16 | 0.25 | 0.85 | 0.43 |
| Reference example 1 | Developer 18 | Not used | Unprinted portion | 0.05 | 0.06 | 0.07 | 0.05 | 0.07 | 0.07 |
| | | | Printed portion | 1.35 | 1.32 | 1.18 | 0.60 | 0.08 | 0.08 |
| Reference example 2 | Developer 19 | Not used | Unprinted portion | 0.05 | 0.05 | 0.06 | 0.06 | 0.08 | 0.06 |
| | | | Printed portion | 1.25 | 1.24 | 1.20 | 0.81 | 0.51 | 0.08 |

Example 29

The same operations as in Example 1 were carried out except that N-(m-tolylaminocarbonyl)-phenylalanine (Developer 1) in Liquid B of Example 1 was replaced with N-(3-isopropenyl-α,α-dimethylbenzyl) amino carbonyl-methionine (Developer 20).

The various test results of the heat-sensitive recording material according to this Example are as shown in Table 4.

TABLE 4

| | Developer | | Coloring density | Moisture resistance | Heat resistance | Oil resistance |
|---|---|---|---|---|---|---|
| Example 29 | Developer 20 | Unprinted portion | 0.05 | 0.06 | 0.05 | 0.08 |
| | | Printed portion | 1.00 | 0.78 | 0.70 | 0.36 |

As is clear from the Examples and Tables 2, 3, and 4, the heat-sensitive recording materials prepared from amino acid derivatives exhibit a good coloring density with high whiteness, and in particular, in the case of Z being an OH group, X being —NHCO—, and the N-substituted amino acid derivative being N-(m-tolylaminocarbonyl)-phenylalanine, N-(m-tolylaminocarbonyl)-methionine, N-(m-tolylaminocarbonyl)-valine, N-(m-tolylaminocarbonyl)-phenylglycine, and N-(m-tolylaminocarbonyl)-tyrosine, the prepared heat-sensitive recording materials also exhibit good storage stability in terms of the heat resistance, moisture resistance, and oil resistance of the printed portions and unprinted portions, in addition to exhibit good coloring density with a high whiteness. In addition, it is possible to obtain a heat-sensitive recording material which is also excellent in water resistance of the printed portion by adding a specific storage stabilizer.

INDUSTRIAL APPLICABILITY

The developer used in the heat-sensitive recording material of the present invention has a natural amino acid as a main raw material, and for this reason, there is no concern regarding endocrine disruption, the superior coloring density is exhibited, the whiteness of non-printed portion is high, and the storage stability of the printed portion is also good, thus the industrial applicability as an alternative to the heat-sensitive recording materials of the related art is extremely promising.

What is claimed is:
1. A heat-sensitive recording material comprising:
    a heat-sensitive recording layer containing a basic dye which is colorless or light-colored at room temperature and a developer capable of expressing a color through contact with the dye by heating and provided on a supporting body,
    wherein the developer is at least one type of an N-substituted amino acid derivative represented by the following General Formula (1):

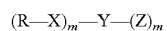

(1)

in Formula (1), R represents an alkyl group having an aryl group having 6 to 10 carbon atoms, or an aryl group which may have a substituent of an alkyl group having 1 to 8 carbon atoms, an aralkyl group having 7 to 11 carbon atoms, an aryl group having 6 to 10 carbon atoms, or an alkoxy group having 1 to 8 carbon atoms, X is a group bonded to an N-terminus of Y and represents —OCO—, —SO$_2$NHCO—, —NHCO—, —NHCS—, or —SO$_2$—, Y represents an amino acid residue or a peptide residue and an OH group of a serine residue, a threonine residue, an aspartic acid residue, a glutamic acid residue, or a tyrosine residue in the Y group may be substituted with an OR group or an OR" group, an SH group of a cysteine residue may be substituted with an SR group or an SR" group, an NH group of a histidine residue may be substituted with an NR group or an NR' group, an NH$_2$ group of a lysine residue or an ornithine residue may be substituted with an NHR group or an NHR' group, R' represents an amino protecting group, and R" represents a carboxy protecting group, Z is a group bonded to a C-terminus of Y and represents an OH group or an OR" group, and a plurality of R, R', and R" groups may be the same as or different from each other and may be bonded to each other to form a ring, with the proviso that Y is an amino acid residue other than a cystine residue or a peptide residue not having a cystine residue, and m=1.

2. The heat-sensitive recording material according to claim 1, wherein said developer is at least one type selected from the group consisting of N-(m-tolylaminocarbonyl)-phenylalanine, N-(m-tolylaminocarbonyl)-methionine, N-(p-tolylaminocarbonyl)-methionine, N-(phenylaminocarbonyl)-methionine, N-(m-tolylaminocarbonyl)-valine, N-(m-tolylaminocarbonyl)-phenylglycine, and N-(m-tolylaminocarbonyl)-tyrosine.

3. The heat-sensitive recording material according to claim 1, wherein said heat-sensitive recording layer contains, as a storage stabilizer, at least one type or more selected from 1,1,3-tris(2-methyl-4-hydroxy-5-tert-butylphenyl)butane, 1,1,3-tris(2-methyl-4-hydroxy-5-cyclohexylphenyl)butane, 4,4'-bis[(4-methyl-3-phenoxycarbonylaminophenyl)ureido]diphenylsulfone, and a diphenylsulfone cross-linking type compound represented by the following General Formula (2):

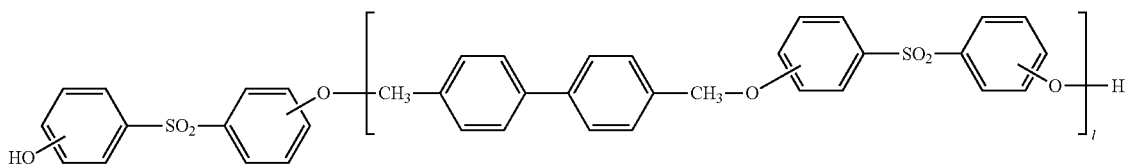

(2)

in the formula, l represents an integer of 1 to 6.

4. The heat-sensitive recording material according to claim 3, wherein an amount of said storage stabilizer ranges from 2.5 to 100 parts by mass with respect to 100 parts by mass of said developer.

* * * * *